United States Patent [19]

Kunz et al.

[11] Patent Number: 5,578,339

[45] Date of Patent: Nov. 26, 1996

[54] SWEETENER, PROCESS FOR ITS PREPARATION AND THE USE THEREOF

[75] Inventors: Markwart Kunz, Braunschweig; Hanspeter Degelmann, Worms; Wolfgang Wach, Braunschweig; Mohammad Munir, Kindenheim; Jörg Kowalczyk, Grünstadt; Manfred Vogel, Neuleiningen, all of Germany

[73] Assignee: Südzucker Aktiengesellschaft Mannheim/Ochsenfurt, Mannheim, Germany

[21] Appl. No.: 238,692

[22] Filed: May 5, 1994

[30] Foreign Application Priority Data

May 6, 1993 [DE] Germany .................. 43 14 961.8
Dec. 27, 1993 [EP] European Pat. Off. .............. 93120934

[51] Int. Cl.$^6$ .................... A23L 1/236; C12P 19/12; C12P 19/18; C12P 41/00
[52] U.S. Cl. .................... 426/658; 127/36; 435/280; 435/276; 435/880; 435/847; 435/874; 435/41; 426/577; 426/660
[58] Field of Search ................... 426/658, 577, 426/660; 127/36; 435/280, 276, 880, 847, 874, 41

[56] References Cited

U.S. PATENT DOCUMENTS

| | | |
|---|---|---|
| 3,865,957 | 2/1975 | Schiweck et al. . |
| 3,912,804 | 10/1975 | Schiweck . |
| 3,940,481 | 2/1976 | Schiweck . |
| 4,117,173 | 9/1978 | Schiweck et al. . |
| 4,670,387 | 6/1987 | Bucke et al. . |
| 4,684,720 | 8/1987 | Darsow et al. . |
| 4,788,145 | 11/1988 | Munir . |
| 5,229,276 | 7/1993 | Sugitani et al. . |

FOREIGN PATENT DOCUMENTS 1185551 4/1985 Canada .
1429334 3/1976 United Kingdom .

OTHER PUBLICATIONS

Inoue Yoshinori et al., "Cation–Exchange Resin, and Separation of Saccharide and Sugar–Alcohol Using Said Resin," Patent Abstracts of Japan Pub. No. 59–162953, vol. 9 No. 12 (C–261) (1735) Sep. 13, 1994.

Munir et al., "1–O–alpha–D–Glucopyranosyl–D–fructuose: Darstellung aus Saccharose und ihre Reduktion zu 1–O–alpha–D–Gloucopyranosyl–D–glucitol," Carbohydrate Res., Bd. 164 (1987) pp. 477–485.

Schiweck, "Herstellung, technologische Eigenschaften und Analytik palatinithaltiger Lebensmittel," Alimenta, Bd. 19, No. 1 (1980) pp. 5–16.

Primary Examiner—Esther Kepplinger
Assistant Examiner—Choon P. Koh
Attorney, Agent, or Firm—Finnegan, Henderson, Farabow, Garrett & Dunner, L.L.P.

[57] ABSTRACT

A process for the preparation of a sweetener, in which sucrose is converted enzymatically into a saccharide mixture which is called "isomerized sucrose" and has a disaccharide content of more than 85% by weight, then non-isomerized remaining sucrose is removed from the latter by enzymatic and/or $H^+$ ion-catalyzed cleavage, and this product is catalytically hydrogenated. Preferably either before or after the catalytic hydrogenation, the resulting mixture is subjected to a chromatographic separation. The sweeteners prepared by this process contain either a mixture of 10 to 50% by weight of 6-O-α-D-glucopyranosyl-D-sorbitol; 2 to 20% by weight of 1-O-α-D-glucopyranosyl-D-sorbitol; and 30 to 70% by weight of 1-O-α-D-glucopyranosyl-D-mannitol or of 5 to 10% by weight of 6-O-α-D-glucopyranosyl-D-sorbitol; 30 to 40% by weight of 1-O-α-D-glucopyranosyl-D-sorbitol; and 45 to 60% by weight of 1-O-α-D-glucopyranosyl-D-mannitol.

23 Claims, No Drawings

SWEETENER, PROCESS FOR ITS PREPARATION AND THE USE THEREOF

BACKGROUND OF THE INVENTION

The invention relates to a novel sweetener, to a process for the preparation thereof and to the use of this sweetener in foodstuffs and other consumables.

Since sucrose is a high-calorie foodstuff, promotes dental caries and is unsuitable for diabetics, there is a need for other sweeteners which, in contrast to synthetic sweetening substances such as saccharin, cyclamate or aspartame, have no additional taste and have bodying properties.

Sweeteners which have been proposed to date as non-cariogenic, low-calorie sweeteners are, inter alia, maltitol and lactitol as well as isomaltitol. The former have only limited uses because of their syrupy consistency, while the latter has not to date been prepared in an economic manner.

Isomaltitol can be obtained, for example, as described in DE 22 17 628 A1 via isomaltulose as intermediate with subsequent catalytic hydrogenation. The yield of the intermediate isomaltulose is only 45%, and the overall yield of isomaltitol is 41%.

Although according to EP 28 900 A1, EP 49 472 A1 and EP 91 063 A1 it is possible with immobilized bacterial cells to bring about enzymatic conversion of sucrose into isomaltulose in a yield of about 80%, purified isomaltulose is required to prepare isomaltitol so that in this process a reduction in yield also occurs due to crystallization.

Furthermore, isomaltitol has the disadvantage that, because of its low solubility, it tends to crystallize out in food products which leads, for example, to chocolate having a sandy taste, hard candies becoming cloudy and crystals forming in jams.

Furthermore, DE 25 20 173 A1 discloses that catalytic reduction of isomaltulose in neutral aqueous solution results not only in isomaltitol, that is to say glucopyranosyl-1,6-sorbitol (=1,6-GPS), but also in the stereoisomeric glucopyranosyl-1, 6-mannitol (=1, 6-GPM) up to a ratio of 1:1 by weight. It is true that 1,6-GPM can,. because of its low solubility, be easily isolated and is, as a low-calorie, bodying product, an enrichment of dietetics. However, because of its low solubility it crystallizes out in food products even more readily than isomaltitol and must—because the sweetening power is only about 40% that of sucrose—be employed in a larger amount to achieve the same sweetening effect.

Mixtures of 1,6-GPS or 1,6-GPM with other sugar alcohols or sugars also yield unsatisfactory products. Even on use of sorbitol, which is known to suppress crystallization, the resulting products are hygroscopic, that is to say sticky.

Finally, EP 109 009 A1 describes an isomerization product which was prepared from sucrose with Protaminobacter rubrum (CBS 574.77) and has the following composition by weight of DM (dry matter) content:

| | | |
|---|---|---|
| Fructose | 5–8% | by weight of DM content |
| Glucose | 2–5% | by weight of DM content |
| Sucrose | 0–0.5% | by weight of DM content |
| Isomaltulose | 65–72% | by weight of DM content |
| Trehalulose | 10–20% | by weight of DM content |
| Oligomers | 3–6% | by weight of DM content |

A saccharide mixture of this type is unsuitable as dietetic sweetener because some components are utilized calorically, show insulin-dependent metabolism and promote dental caries. It is true that the trehalulose content can be increased to 35% if the sugar mixture is kept with free or carrier-immobilized bacterial cells under suitable conditions for about 100 h. However, this process is uneconomic.

The invention is therefore based on the object of proposing a sweetener and a process for the preparation of a novel low-calorie, non-cariogenic sweetener which is suitable for diabetics and which combines a pleasant sweetening effect with good bodying properties, can be prepared in solid form easily and economically and does not crystallize out in the concentrations used.

SUMMARY OF THE INVENTION

To achieve this object, a process is provided for the preparation of a sweetener which comprises a) in a first process step converting sucrose enzymatically into isomerized sucrose having a disaccharide content of more than 85% by weight, b) in a second step removing non-isomerized remaining sucrose from the isomerized sucrose by enzymatic or $H^+$-catalyzed cleavage, c) catalytically hydrogenating the isomerized sucrose, and d) either before or after the catalytic hydrogenation subjecting the resulting mixture to chromatographic separation.

In addition, a sweetner is provided which comprises a mixture of 10 to 50% by weight of 6-O-α-D-glucopyranosyl-D-sorbitol;
2 to 20% by weight of 1-O-α-D-glucopyranosyl-D-sorbitol; and
30 to 70% by weight of 1-O-α-D-glucopyranosyl-D-mannitol.
or a mixture of
5 to 10% by weight of 6-O-α-D-glucopyranosyl-D-sorbitol;
30 to 40% by weight of 1-O-α-D-glucopyranosyl-D-sorbitol; and
45 to 60% by weight of 1-O-α-D-glucopyranosyl-D-mannitol.

Finally, these sweeteners can be used in solid or liquid form with foodstuffs and other consumables.

DETAILED DESCRIPTION OF THE INVENTION

The invention is based on the surprising finding that sweeteners with the required properties are obtained by the combination of the process steps of isomerization of sucrose, removal of non-isomerized remaining sucrose and catalytic hydrogenation and, preferably, both by the chromatographic treatment which is carried out either before or after the hydrogenation, and, in particular, by a specific selection of bacterial strains.

The invention is explained in detail hereinafter, using the following abbreviations:

| | | |
|---|---|---|
| 1,6-GPS for 6-O-α-D-glucopyranosyl-D-sorbitol | | |
| 1,1-GPS for 1-O-α-D-glucopyranosyl-D-sorbitol | | |
| 1,1-GPM for 1-O-α-D-Glucopyranosyl-D-mannitol | | |
| and where it should also be stressed that the result of hydrogenation | | |
| of isomaltose is | 100% | 1,6-GPS, |
| of isomaltulose is | 43–57% | 1,1-GPM |
| | 43–57% | 1,6-GPS and |
| of trehalulose is | 50–80% | 1,1-GPM |
| | 20–50% | 1,1-GPS. |

In the process according to the invention, in a first stage sucrose is isomerized with bacterial strains from the group comprising *Protaminobacter rubrum* (CBS 574.77), *Serratia plymuthica* (ATCC 15928), *Serratia marcescens* (NCIB 8285), *Leuconostoc mesenteroides* (NRRL-B 512 F (ATCC 1083 a)) and *Erwinia rhapontici* (NCPPB 1578).

Then, in a second process step, the non-isomerized remaining sucrose is removed from this "isomerized sucrose". This is essential in the present process, although it is known per se to cleave pure sucrose solutions with invertase and/or an inverting resin to a mixture of glucose and fructose; only it was not previously known to carry out a specific cleavage of sucrose in the presence of considerably larger amounts of other disaccharides without impairment thereof.

Then, in a third process step, the "isomerized sucrose" from which the remaining sucrose has been removed is catalytically hydrogenated, resulting in a mixture of the following composition:

| | |
|---|---|
| Mannitol (from fructose) | 3 to 4% by weight |
| Sorbitol (from fructose and glucose) | 4 to 9% by weight |
| 6-O-α-D-Glucopyranosyl-D-sorbitol (= 1,6-GPS) from isomaltulose | 10 to 55% by weight |
| 1-O-α-D-glycopyranosyl-D-sorbitol (= 1,1-GPS) from trehalulose | 2 to 20% by weight |
| 1-O-α-D-Glucopyranosyl-D-mannitol (= 1,1-GPM) from isomaltulose and trehalulose | 30 to 70% by weight |
| Hydrogenated oligosaccharides | 3 to 6% by weight |
| Sucrose | below 1% by weight |

The GPS/GPM ratio is about 2:1 to 1:7, depending on the hydrogenation conditions (alkaline/neutral).

Since the oligosaccharides may have adverse effects on the use properties as well as the physiological properties of the resulting product, they are additionally removed, preferably by chromatographic separation on cation exchange resins or zeolites.

The mixture of sorbitol, mannitol, 1,6-GPS, 1,1-GPS and 1,1-GPM resulting after the chromatographic separation can be used as sweetener in liquid form or else as dry, free-flowing product.

Thus, it is also alternatively possible to remove the remaining sucrose, which cannot be hydrogenated, from the isomerized sucrose and, in particular, to remove glucose, fructose and oligosaccharides, which is effected by chromatographic separation on cation exchange resins or zeolites.

It is advantageous, for better use of the sweetener in food products in which a high dry matter content is to be maintained, to suppress the tendency of 1,1-GPM to crystallize by increasing the 1,1-GPS content. This can be achieved, according to another alternative, by converting sucrose enzymatically with bacteria of the species *Pseudomonas mesoacidophila* or *Agrobacterium radiobacter* in aqueous solution into a mixture of sugars which predominantly consists of trehalulose, and subjecting this mixture of sugars to catalytic hydrogenation and purification. In particular, the bacterial strains *Pseudomonas mesoacidophila* MX-45 (FERM BP 3619) or *Agrobacterium radiobacter* MX-232 (FERM BP 3620) are employed.

In order to convert the resulting sweetener, which is in the form of a liquid mixture of sorbitol, mannitol, 1,6-GPS, 1,1-GPS and 1,1-GPM, into dry form, the water which is present as solvent must be removed by evaporation, it being advantageous previously to reduce the sorbitol and mannitol content to 5 to 0 and preferably to 1 to 0%; this can be carried out by the chromatographic separation on suitable cation exchange resins or zeolites.

The mixtures prepared according to the invention have a sweetness similar to that of sucrose without an additional taste; however, the sweetening power is only 40 to 50%. This can be increased where appropriate by adding synthetic sweetening substances and adjusted, for example, to the sweetening power of sucrose. When used in candies or jam, the resulting body is comparable to that with sucrose, but the individual saccharides do not crystallize out.

EXAMPLE 1

A. Preparation of the biocatalyst

Cells are rinsed off a subculture of the strain *Protaminobacter rubrum* (CBS 574.77) with 10 ml of a sterile nutrient substrate composed of 8 kg of thick juice from a sugar works (dry matter content 65%), 2 kg of corn steep liquor, 0.1 kg of $(NH_4)_2HPO_4$ and 89.9 kg of distilled water, adjusted to pH 7.2 if required. This suspension is used as inoculum for the shaker preculture in 1 liter flasks containing 200 ml of nutrient solution of the above composition.

After an incubation time of 30 hours at 29° C., 18 liters of nutrient solution of the above composition in a 30 liter small fermenter are inoculated with, in each case, 10 flasks (total content 2 liters) and fermented at 29° C. with 20 liters of air per minute and a stirrer speed of 350 rpm.

After the organism counts have reached above $5 \times 10^9$ organisms/ml, the fermentation is stopped, the cells are harvested from the fermenter solution by centrifugation, suspended in a 2% strength sodium alginate solution and immobilized by adding the suspension dropwise to a 2% strength calcium chloride solution.

The resulting immobilisate beads are washed with water. This biocatalyst can be stored at +4° C. for several weeks.

B. Preparation of the "isomerized sucrose"

The immobilized cells obtained as in A are packed in a column reactor which can be thermostatted and are thermostatted at 25° to 30° C., and a sucrose solution with a (dry matter) content of 35 to 45% is passed through continuously. The flow rate in this case is adjusted so that at least 97% of the sucrose employed are rearranged.

HPLC analysis of the "isomerized sucrose" emerging from the column reactor revealed the following composition:

| | |
|---|---|
| Fructose | 2.5% of DM |
| Glucose | 2.0% of DM |
| Sucrose | 1.0% of DM |
| Isomaltulose | 82.5% of DM |
| Trehalulose | 9.5% of DM |
| Isomaltose | 1.5% of DM |
| Oligomers (DP > 3) | 1.0% of DM. |

C. Removal of remaining sucrose

The remaining sucrose, which cannot be hydrogenated, was removed from the "isomerized sucrose" obtained in this way by treating it in a strongly acidic cation exchanger loaded with $H^+$ ions or with suitable enzymes in a column reactor as follows:

i) Removal of the remaining sucrose on strongly acidic cation exchangers 100 cm$^3$ of a strongly acidic cation exchanger (for example Lewatit® OC 1052) were packed in a suitable glass column thermostatted at 60° C. and loaded with H⁺ ions by regeneration with HCl by a known method.

The "isomerized sucrose" obtained in Example 1 B was pumped at a flow rate of 100 cm³·h⁻¹ through the cation exchanger column prepared in this way. The product obtained at the column outlet had the following composition (HPLC):

| | |
|---|---|
| Fructose | 3.0% of DM |
| Glucose | 2.5% of DM |
| Sucrose | |
| Isomaltulose | 82.3% of DM |
| Trehalulose | 9.5% of DM |
| Isomaltose | 1.5% of DM |
| Oligomers (DP > 3) | 1.2% of DM | ii) Removal of the remaining sucrose by enzymes 11 g of an immobilized invertase (for example SP 362 from NOVO NORDISK A/S Copenhagen), corresponding to a bed volume of 33 cm³, were packed in a suitable glass column thermostatted at 60° C.

The "isomerized sucrose" obtained in Example 1 B was pumped at a flow rate of 210 cm³h⁻¹ continuously through this column.

HPLC analysis of the product emerging from the "invertase column" revealed the following composition:

| | |
|---|---|
| Fructose | 3.0% of DM |
| Glucose | 2.5% of DM |
| Sucrose | |
| Isomaltulose | 82.5% of DM |
| Trehalulose | 9.5% of DM |
| Isomaltose | 1.5% of DM |
| Oligomers (DP > 3) | 1.0% of DM |

In both cases, the remaining sucrose was completely cleaved to glucose and fructose. The content of these monosaccharides was correspondingly higher whereas the other components of the "isomerized sucrose" were unchanged.

D. Hydrogenation of the "isomerized sucrose"

Each of the batches of "isomerized sucrose" from which the remaining sucrose had been removed were continuously hydrogenated on Raney nickel at 80° C. with gaseous hydrogen under a pressure of about 10 MPa. After removal of the nickel and purification by ion exchange, the batches of "isomerized sucrose" hydrogenated under neutral conditions had approximately the following composition:

| | |
|---|---|
| Mannitol | 1.5% of DM |
| Sorbitol | 4.0% of DM |
| 1,6-GPS | 44.4% of DM |
| 1,1-GPS | 3.8% of DM |
| 1,1-GPM | 45.3% of DM |
| Hydrogenated and non-hydrogenated oligomers | 1.0% of DM |

Although this product can be employed as sweetener after removal of water by evaporation, it has only limited uses because of its hygroscopicity, particularly because of the oligomer content, especially since the oligomers still present are partially cleaved in the small intestine to liberate sorbitol, mannitol and, in particular, glucose and fructose and thus are problematic in diabetic food products.

EXAMPLE 2

"Isomerized sucrose" was prepared in analogy to Example 1 A to C and was subjected to a chromatographic separation treatment to remove glucose, fructose and oligosaccharides before the hydrogenation, the intention being simultaneously to avoid a loss of the disaccharides isomaltulose, isomaltose and trehalutose.

The chromatographic separating column used was a tube with a length of 10 m and a diameter of 25 cm which was thermostatable and provided with a perforated plate and which was completely filled with water and subsequently charged with a strongly acidic cation exchange resin which was loaded with calcium ions and had 4 to 6% crosslinking and a particle size of about 0.4 to 0.5 mm in such a way that the resin was completely covered with water.

The "isomerized sucrose" obtained as in Example 1 A and B was, after removal of the remaining sucrose, loaded in an amount of about 18 kg (dry matter) onto the separating column which was thermostatted at about 75° C. and was eluted with deionized water at a flow rate of about 2 cm/min. Fractions were collected every 10 minutes at the outlet from the separation column and their composition was investigated by HPLC.

The first four fractions contained about 60% of the oligosaccharides and, in addition, about 10% of the isomaltulose and about 25% of the isomaltose. The last five fractions contained about 70% of the fructose, 10% of the trehalulose and 20% of the glucose.

The composition of the resulting "isomerized sucrose" was as follows:

| | |
|---|---|
| Fructose | 1.0% of DM |
| Glucose | 2.3% of DM |
| Isomaltulose | 85.1% of DM |
| Trehalulose | 9.8% of DM |
| Isomaltose | 1.3% of DM |
| Oligomers | 0.5% of DM |

It is nevertheless possible by this type of separation to remove about 60% of the oligomers, 70% of the fructose and 20% of the glucose, but loss of 10% of the isomaltulose, 10% of the trehalulose and 25% of the isomaltose must be accepted.

The resulting product was hydrogenated in analogy to Example 1 D and had the following composition:

| | |
|---|---|
| Mannitol | 0.5% of DM |
| Sorbitol | 3.3% of DM |
| 1,6-GPS | 43.8% of DM |
| 1,1-GPS | 3.9% of DM |
| 1,1-GPM | 48.5% of DM |
| Oligomers | 0.5% of DM |

The content of sorbitol and mannitol was lower than in the product of Example 1; the content of hydrogenated and non-hydrogenated oligomers was only one half.

EXAMPLE 3

The process was analogous to Example 2 but this time the separating column was charged with a zeolite which had an Si/Al ratio of about 50.

The first five fractions contained the total amount of oligosaccharides, glucose and fructose and about 50% of the isomaltose too. These fractions contained neither trehalulose nor isomaltulose. Since the isomaltose content of the "isomerized sucrose" from Example 1 and 2 is 1.5 and 1.3% of DM respectively, with this procedure only about 0.8 and 0.5%, respectively, of the required disaccharides is lost. At the same time, the unwanted oligosaccharides, glucose and fructose are completely removed.

The resulting "isomerized sucrose" had the following composition:

| | |
|---|---|
| Fructose | — |
| Glucose | — |
| Isomaltulose | 89.0% of DM |
| Trehalulose | 10.2% of DM |
| Isomaltose | 0.8% of DM |
| Oligomers | — |

This product was hydrogenated in analogy to Example 1 D and showed the following composition:

| | |
|---|---|
| 1,6-GPS | 45.3% of DM |
| 1,1-GPS | 4.1% of DM |
| 1,1-GPM | 50.6% of DM |

This product from which mannitol, sorbitol and oligomers had been removed was an excellent sweetener which was scarcely hygroscopic and was suitable for diabetics.

EXAMPLE 4

The "isomerized sucrose" which had been obtained as in Example 1 and was already hydrogenated was treated with a chromatographic separating column as used in Example 2 before the hydrogenation, analogously loading on about 18 kg of DM of the now hydrogenated "isomerized sucrose" and eluting at a flow rate of 2 Cm/min. However, this separating column was now charged with a strongly acidic cation exchange resin loaded with sodium ions.

The first three fractions contained the oligomers and about 4% of the 1,1-GPM. The subsequent fractions 4 to 8 contained the remaining amount of 1,1-GPM, the total amount of 1,1-GPS and about 99% of the 1,6-GPS, as well as about 50% of the mannitol and only small amounts of the sorbitol. It is evident from the mass balances that the product of fractions 4 to 8 has a total GPM and GPS content of about 97% by weight. The remaining amounts of 1,6-GPS, mannitol and sorbitol were eluted in fraction 9 and following fractions.

Compared with the process of Example 2, in which the chromatographic separation was carried out with cation exchangers loaded with alkaline earth metal, there is a better separation between disaccharide and monosaccharide alcohols, so that more than 97% by weight of the required disaccharide alcohols can be obtained in the main product, whereas the yield is about 85% with cation exchangers loaded with calcium ions. The further advantage which surprisingly also emerges is that more than 90% of the sorbitol, which is produced as utilizable byproduct, can be obtained with a purity of more than 98%.

The composition of the product was as follows:

| | |
|---|---|
| 1,6-GPS | 46.2% of DM |
| 1,1-GPS | 4.1% of DM |
| 1,1-GPM | 49.6% of DM |

EXAMPLE 5

A chromatographic separation was carried out in analogy to Example 4 after the hydrogenation, but now using a zeolite separation system as in Example 3. Hydrogenated "isomerized sucrose" was loaded in an amount of 15 to 20 kg (dry matter) and eluted with deionized water.

Analysis of the resulting fractions shows that mannitol, sorbitol and oligomers are completely present in the first 5 fractions. They additionally contain about 5% of the amount of GPM. The remaining GPM, all the 1,1-GPS and 1,6-GPS are recovered in fractions 6 to 16.

It is thus possible to obtain more than 97% of the required disaccharide alcohols free of sorbitol, mannitol and oligomers.

EXAMPLE 6

To crystallize the fractions containing the disaccharide alcohols, very generally the water content is removed by evaporation. To do this, these fractions, for example the fraction obtained as in Example 5, were concentrated to a dry matter content of 90 to 95% by evaporation under reduced pressure, allowed to solidify on a cooled surface and subsequently ground. A fine-particle, non-adhesive and free-flowing product was obtained.

If the sweetener is to be employed in food products with a high dry matter content, it is advantageous to suppress the tendency of 1,1-GPM to crystallize by increasing the 1,1-GPS. This is achieved with another type of bacterial strains, as the following example shows.

EXAMPLE 7

To prepare this biocatalyst, cells were rinsed off a subculture of the strain *Pseudomonas mesoacidophila* MX-45 (FERM BP 3619) with 10 ml of a sterile nutrient substrate composed of 8 kg of thick juice from a sugar works (dry matter content=65%), 2 kg of corn steep liquor, 0.1 kg of $(NH_4)_2HPO_4$ and 89.9 kg of distilled water, adjusted to pH 7.2 if required. This suspension was used as inoculum for a shaker preculture in a 1 liter flask containing 200 ml of the nutrient solution.

After incubation at 29° C. for 30 hours, 18 liters of nutrient solution of the above composition in a 30 liter small fermenter were inoculated with, in each case, 10 flasks (total content 2 liters) and fermented at 29° C. with 20 liters of air per minute and a stirrer speed of 350 rpm.

After the organism counts had reached above $5 \times 10^9$ organisms/ml, the fermentation was stopped, the cells were harvested from the fermenter solution by centrifugation, suspended in a 2% strength sodium alginate solution and immobilized by adding the suspension dropwise to a 2% strength calcium chloride solution. The resulting immobilisate beads were washed with water. This biocatalyst can be stored at +4° C. for several weeks.

To prepare "isomerized sucrose" the immobilized cells of *Pseudomonas mesoacidophila* MX-45 (FERM BP 3619) obtained in this way were packed in a column reactor which can be thermostated and were thermostatted at about 25° to 30° C., and a sucrose solution with a DM content of about 35 to 45% was passed through continuously. The flow rate in this case was adjusted so that at least 97% of the sucrose employed were rearranged.

HPLC analysis of the "isomerized sucrose" emerging from the column reactor revealed the following composition:

| | |
|---|---|
| Fructose | 0.2% of DM |
| Glucose | 0.2% of DM |

| | |
|---|---|
| Sucrose | 1.0% of DM |
| Isomaltulose | 12.5% of DM |
| Isomaltose | 0.2% of DM |
| Trehalulose | 85.7% of DM |
| Oligomers (DP > 3) | 0.2% of DM |

In analogy to Example 1, initially the remaining sucrose which cannot be hydrogenated was removed from the "isomerized sucrose" prepared in this way, and the latter was continuously hydrogenated on Raney nickel at about 80° C. with gaseous hydrogen under a pressure of 8 to 12 MPa.

After removal of the nickel and purification by ion exchange, the "isomerized sucrose" hydrogenated under neutral conditions had the following composition:

| | |
|---|---|
| Mannitol | 0.4% of DM |
| Sorbitol | 1.0% of DM |
| 1,1-GPM | 57.7% of DM |
| 1,1-GPS | 34.4% of DM |
| 1,6-GPS | 6.4% of DM |
| Hydrogenated and non hydrogenated oligomers | 0.2% of DM |

In order to remove the hydrogenated and nonhydrogenated oligomers and the sorbitol from the product by chromatographic separation, the chromatographic separation after the hydrogenation was carried out with a chromatographic separating column as in Example 4, that is to say with a strongly acidic cation exchange resin loaded with sodium or potassium ions.

Analysis of the resulting fractions shows that the first 3 fractions contain the oligomers and about 4% of the GPM. Fractions 4 to 8 contain the remaining GPM, all the 1,1-GPS and about 99% of the 1,6-GPS as well as about 50% of the mannitol. The remaining 1,6-GPS as well as the sorbitol and mannitol are eluted in fractions No. 9 and thereafter.

EXAMPLE 8

To establish the relative sweetening power, the following solutions were compared with one another in a triangle test with 15 testers in each case:

a) Two 7% strength sucrose solutions versus a 15.5% strength solution of the novel sweetener according to Example 3.

b) Two 7% strength sucrose solutions versus a 17.5% strength solution of this novel sweetener.

c) Two 7% strength sucrose solutions versus an 18.5% strength solution of this novel sweetener.

In test a), six people identified the novel sweetener: no statistically verified difference from the sucrose solutions.

In test b), twelve people identified the novel sweetener as "sweeter": statistically verified difference with $p=0.99$.

In test c), likewise twelve people identified the novel sweetener as "sweeter": statistically verified difference with $p=0.99$.

The sweetening power of the sweetener according to the invention is 45% of that of sucrose. To increase the sweetening power, the new sweetener can be mixed with fructose, xylitol, saccharin, cyclamate, aspartame or acesulfame-K.

EXAMPLE 9

To produce ice cream with the novel sweetener, 22.1 kg of dairy cream (40% fat in dry matter), 58.1 kg of whole milk (3.7% fat in DM) and 4.5 kg of skim milk powder were mixed with 15 kg of the sweetener of Example 3 and 0.3 kg of stabilizer, homogenized and sterilized.

After the sterilization, 53 g of finely ground methyl phenylalanylaspartate were added to the ice composition, stirred, whipped and frozen. The product has the same sweetness and the same taste as ice cream produced with 15 kg of sugar.

In the case of fruit ice cream it is in fact advantageous to dispense with additional sweetening because the novel sweetener brings out the taste of the fruit considerably better.

EXAMPLE 10

To produce a low-calorie strawberry jam, 1 kg of chopped strawberries was boiled together with 1 kg of the novel sweetener of Example 3 and 8 g of a medium-esterified pectin with 150° SAG-USA (Ullmann, Enzyklopädie der technischen Chemie, 3rd edition, vol. 13, page 180) and 7 g of tartaric acid for three minutes and bottled in prepared bottles.

Comparison with a jam produced with sugar showed no difference in consistency, the sweetness was somewhat less but this was compensated by the strawberry taste being detectably stronger. After storage for a period of six months, the sweetener showed no tendency to crystallize.

We claim:

1. A process for the preparation of a sweetener comprising 6-O-α-D-glucopyranosyl-D-sorbitol (1,6-GPS), 1-O-α-D-glucopyranosyl-D-sorbitol (1,1-GPS), and 1-O-α-D-glucopyranosyl-D-mannitol (1,1-GPM), comprising the steps of a) converting sucrose enzymatically into isomerized sucrose having a disaccharide content by weight of more than 85% of disaccharides of the group consisting of isomaltulose, trehalulose, and isomaltose and less than 15% by weight of monosaccharides of the group consisting of glucose and fructose and of non-converted sucrose and oligomers;

b) removing non-isomerized remaining sucrose from the isomerized sucrose by enzymatic or $H^+$-catalyzed cleavage;

c) catalytically hydrogenating the isomerized sucrose; and d) either before or after the catalytic hydrogenation subjecting the resulting mixture to chromatographic separation to prepare said sweetner.

2. The process as claimed in claim 1, wherein the chromatographic separation removes oligosaccharide alcohols or monosaccharide alcohols contained in the mixture using strongly acidic cation exchange resins loaded with sodium, potassium or calcium ions or on zeolites with an Si/Al ratio >50.

3. A sweetener which comprises a mixture of 10 to 50% by weight of 6-O-α-D-glucopyranosyl-D-sorbitol (1,6-GPS);

2 to 20% by weight of 1-O-α-D-glucopyranosyl-D-sorbitol (1,1-GPS); and 30 to 70% by weight of 1-O-α-D-glucopyranosyl-D-mannitol (1,1-GPM).

4. A sweetener as claimed in claim 3, which comprises 25 to 50% by weight 6-O-α-D-glucopyranosyl-D-sorbitol (1,6-GPS);

2 to 20% by weight of 1-O-α-D-glucopyranosyl-D-sorbitol (1,1-GPS); and 35 to 60% by weight of 1-O-α-D-glucopyranosyl-D-mannitol (1,1-GPM).

5. A sweetener which comprises a mixture of 5 to 10% by weight of 6-O-α-D-glucopyranosyl-D-sorbitol (1,6-GPS);

30 to 40% by weight of 6-O-α-D-glucopyranosyl-D-sorbitol (1,1-GPS); and 45 to 60% by weight of 1-O-α-D-glucopyranosyl-D-mannitol (1,1-GPM).

6. The sweetener of claim 3, which contains small amounts of mannitol, sorbitol, hydrogenated or non-hydrogenated oligosaccharides, or mixtures thereof.

7. A method for sweetening foodstuffs which comprises adding an effective amount to achieve a sweetened effect of the sweetener of claim 3.

8. The sweetener of claim 5, which contains small amounts of mannitol, sorbitol, hydrogenated or non-hydrogenated oligosaccharides or mixtures thereof.

9. A method for sweetening foodstuffs which comprises adding an effective amount of the sweetener of claim 5 to achieve a sweetened effect.

10. A process for the preparation of a sweetener comprising 6-O-α-D-glucopyranosyl-D-sorbitol (1,6-GPS), 1-O-α-D-glucopyranosyl-D-sorbitol (1,1-GPS), and 1-O-α-D-glucopyranosyl-D-mannitol (1,1-GPM), comprising the steps of:
a) converting sucrose enzymatically with bacteria selected from the group of species consisting of *Protaminobacter rubrum, Serratia plymuthica, Serratia marcescens, Leuconostoc mesenteroides*, and *Erwinia rhapontici* into isomerized sucrose having a content of more than 85% by weight of disaccharides of the group consisting of isomaltulose, trehalulose, and isomaltose and less than 15% by weight of monosaccharides of the group consisting of glucose and fructose and of non-converted sucrose and oligomers;
b) removing non-isomerized remaining sucrose from the isomerized sucrose by enzymatic or H$^+$-catalyzed cleavage;
c) catalytically hydrogenating the isomerized sucrose;
d) either before or after the catalytic hydrogenation subjecting the resulting mixture of disaccharides, monosaccharides, and oligomers to chromatographic separation; and
e) isolating the mixture as claimed in claim 3.

11. The process as claimed in claim 10, wherein said bacteria are selected from the group of bacterial strains consisting of *Protaminobacter rubrum* (CBS 574.77), *Serratia phymuthica* (ATCC 15928), *Serratia marcescens* (NCIB, 8285), *Leuconostoc mesenteroides* (NRRL-B 512 F (ATCC 1083a)) and *Erwinia rhapontici* (NCPPB 1578).

12. The process of claim 10 wherein said chromatographic separation step is performed before said catalytic hydrogenation step.

13. The process of claim 10 wherein said chromatographic separation step is performed after said catalytic hydrogenation step.

14. The process as claimed in claim 10, wherein the chromatographic separation removes oligosaccharide alcohols or monosaccharide alcohols contained in the mixture using strongly acidic cation exchange resins loaded with sodium, potassium, or calcium ions or on zeolites with an Si/Al ratio >50.

15. A process for the preparation of a sweetener comprising 6-O-α-D-glucopyranosyl-D-sorbitol (1,6-GPS), 1-O-α-D-glucopyranosyl-D-sorbitol (1,1-GPS), and 1-O-α-D-glucopyranosyl-D-mannitol (1,1-GPM), comprising the steps of:
a) converting sucrose enzymatically with bacteria selected from the group of species consisting of *Pseudomonas mesoacidophila* and *Agrobacterium radiobacter* into isomerized sucrose having a content of more than 85% by weight of disaccharides of the group consisting of isomaltulose, trehalulose, and isomaltulose and less than 15% by weight of monosaccharides of the group consisting of glucose and fructose and of non-converted sucrose and oligomers;
b) removing non-isomerized remaining sucrose from the isomerized sucrose by enzymatic or H$^+$-catalyzed cleavage;
c) catalytically hydrogenating the isomerized sucrose;
d) either before or after the catalytic hydrogenation subjecting the resulting mixture of disaccharides, monosaccharides, and oligomers to chromatographic separation; and
e) isolating the mixture as claimed in claim 5.

16. The process as claimed in claim 15, wherein the enzymatic conversion of the sucrose is carried out with bacterial strains selected from the group consisting of *Pseudomonas mesoacidophila* MX-45 (FERM 3619) and *Agrobacterium radiobacter* MX-232 (FERM 3620).

17. The process of claim 15 wherein said chromatographic separation step is performed before said catalytic hydrogenation step.

18. The process of claim 15 wherein said chromatographic separation step is performed after said catalytic hydrogenation step.

19. The process as claimed in claim 15, wherein the chromatographic separation removes oligosaccharide alcohols or monosaccharide alcohols contained in the mixture using strongly acidic cation exchange resins loaded with sodium, potassium, or calcium ions or on zeolites with an Si/Al ratio >50.

20. Jam comprising the sweetener of claim 3.

21. Candy comprising the sweetener of claim 5.

22. Candy comprising the sweetener of claim 3.

23. Jam comprising the sweetener of claim 5.

* * * * *